(12) United States Patent
Jansen et al.

(10) Patent No.: US 6,830,561 B2
(45) Date of Patent: Dec. 14, 2004

(54) CATHETER WITH PROTECTIVE SLEEVE

(75) Inventors: Lex P. Jansen, Pleasanton, CA (US); Stanley W. Olson, Jr., San Ramon, CA (US); Robert M. Abrams, Los Gatos, CA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 232 days.

(21) Appl. No.: 10/142,575

(22) Filed: May 8, 2002

(65) Prior Publication Data

US 2003/0212411 A1 Nov. 13, 2003

(51) Int. Cl.[7] .............................................. A61M 5/32
(52) U.S. Cl. ...................................... 604/163; 604/171
(58) Field of Search ................................ 604/158, 159, 604/163, 199, 164.01, 171, 164.08, 164.09, 165.01, 165.02

(56) References Cited

U.S. PATENT DOCUMENTS

| | | |
|---|---|---|
| 3,867,937 A | 2/1975 | Schwartz |
| 4,573,981 A | 3/1986 | McFarlane |
| 5,370,623 A | 12/1994 | Kreamer |
| 5,586,968 A | 12/1996 | Grundl et al. |
| 5,662,703 A | 9/1997 | Yurek et al. |
| 5,730,754 A | 3/1998 | Obenchain |
| 6,059,813 A | 5/2000 | Vrba et al. |

OTHER PUBLICATIONS

U.S. patent application Ser. No. 2001/0044595 A1, Reydel, et al "Introducer Apparatus with Eversible Sleeve", publication date Nov. 22, 2001.
U.S. patent application Ser. No. 2003/0105508 A1, Johnson, et al "Everting Balloon Stent Delivery System Having Tapered Leading Edge", publication date Jun. 5, 2003.

*Primary Examiner*—Anhtuan T. Nguyen
(74) *Attorney, Agent, or Firm*—Bingham McCutchen, LLP

(57) ABSTRACT

A device for accessing the spinal canal of a patient includes an introducer and a protective sleeve that is attached at one end thereof to a proximal end of the introducer. The protective sleeve has an outer stationary portion and an inner moveable portion. The outer and inner portions of the protective sleeve are separated by a crown region. A catheter is disposed inside the protective sleeve. During operation, the protective sleeve is advanced within the spinal canal to form a protective barrier between the catheter and the spinal cord. The catheter is advanced and retracted within the protective sleeve.

18 Claims, 4 Drawing Sheets

CATHETER WITH PROTECTIVE SLEEVE

FIELD OF THE INVENTION

The field of the invention relates to devices and methods for accessing the spinal canal and structures of the brain. Specifically, the invention relates to a catheter device and methods of use for traversing the vasculature or spinal canal of a patient to access distal regions of the spinal canal and the brain.

BACKGROUND OF THE INVENTION

In extant neurointerventional procedures, there are essentially two-methods to access the brain and intracranial structures: Open (Craniotomy) and Minimally Invasive (Endovascular or Endolumenal). The open approach is surgical through a craniotomy (perforation). This is an invasive procedure.

A second approach uses minimally invasive endovascular or endolumenal techniques to access the vasculature or structures of the brain. In this procedure, a catheter or similar device is inserted, tracking its way through an artery or other navigable lumen into the anatomical treatment site. Depending on the nature and scope of the disease and the overall health of the patient, this navigation and placement of the access and delivery device and therapeutic modality can be very challenging. The opportunity for prolonged procedures and iatrogenic episodes is real as a lumen or canal may be congenitally, pathologically or traumatically compromised and tortuous. Most procedures require the serial introduction and reintroduction of a number of devices to complete an optimal medical intervention. Tissues within the patient are subjected to repetitive contact with access, delivery and therapeutic devices, including the insults of tissue dissection, resection and friction. Transient, permanent, catastrophic and fatal injury may occur.

Accordingly, there is a need for a device and method that is capable of introducing a catheter or similar device into the spinal canal that minimizes or eliminates the risk of patient injury. The device and method would permit a physician to access regions of the spinal canal and brain that were heretofore impossible or difficult to reach using convention endovascular or endolumenal techniques.

SUMMARY OF THE INVENTION

In a first aspect of the invention, a device for accessing the spinal canal of a patient includes an introducer, a protective sleeve, and a catheter. The protective sleeve has one end thereof attached to the distal end of the introducer, the sleeve having an outer stationary portion and an inner moveable portion. A catheter is disposed within the protective sleeve adjacent to the moveable portion.

In another aspect of the invention, an advancement mechanism is provided for advancing the protective sleeve within the spinal canal at a rate that is at least twice the rate of advancement of the catheter.

In another aspect of the invention, a device for accessing the spinal canal of a patient includes an introducer, a protective sleeve, and a catheter. The protective sleeve has one end thereof attached to the distal end of the introducer. The protective sleeve projects distally from the introducer and includes a moveable crown region at the distal end of the protective sleeve. A catheter is disposed within the protective sleeve.

In still another aspect of the invention, a method of traversing the spinal canal with a catheter includes the steps of deploying a protective sleeve within a portion of the spinal canal and advancing a catheter within the protective sleeve through the portion of the spinal canal.

It is an object of the invention to provide a device having a protective sleeve that forms a stationary barrier between a patient's spinal cord and a moveable catheter. It is another object of the invention to provide a catheter device that can reach the vasculature of brain through the ventrical and the subarachnoid space using the spinal canal as an access route. It is another object of the invention to provide a method of efficiently and safely traversing the spinal canal with a catheter.

DETAILED DESCRIPTION OF THE PREFERRED EMBODIMENTS

Figure 1:
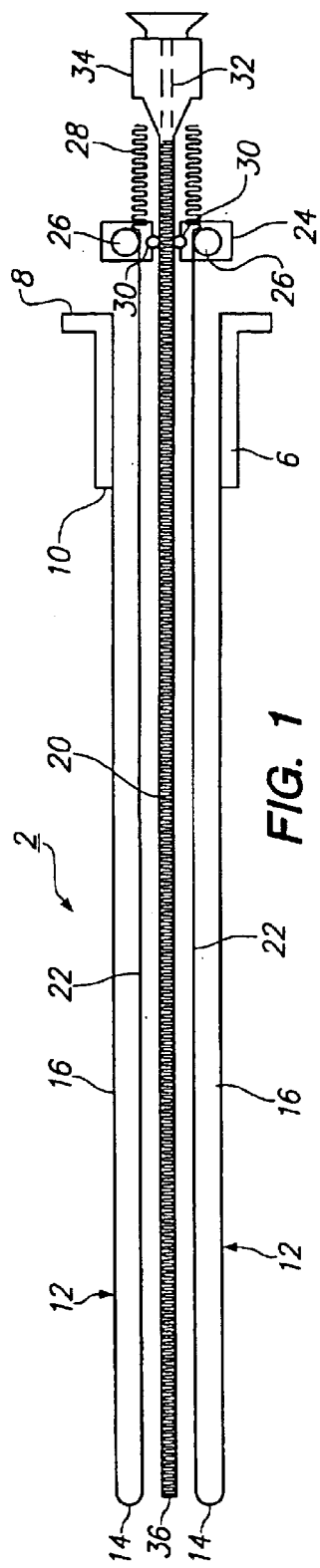
FIG. 1 is a side cross-sectional view of a device for accessing the spinal canal.

FIG. 1 shows one preferred embodiment of the medical device 2 for accessing the spinal canal 4 (shown in FIGS. 10 and 11) of a patient. The device 2 includes an introducer 6 that has a proximal end 8 and a distal end 10. A protective sleeve 12 is attached to the distal end 10 of the introducer 6. The protective sleeve 12 is preferably made of flexible material that permits the protective sleeve 12 to fold back onto itself as is described in more detail below. The protective sleeve 12 may or may not be made of a biocompatible material because the device 2 is not likely to be in the patient's body for an extended period of time.

The protective sleeve 12 projects distally from the introducer 6 in the shape of a tube until it reaches a crown region 14. As seen in FIG. 1, the portion of the protective sleeve 12 between the distal end 10 of the introducer 6 and the crown region 14 is the outer sleeve portion 16 that, during deployment, acts as a stationary barrier between the spinal cord 18 (shown in FIGS. 10 and 11) and the catheter 20 disposed inside the unfurled protective sleeve 12. The protective sleeve 12 also includes a moveable inner sleeve portion 22 between the crown region 14 and the end of the protective sleeve 12 that is not attached to the distal end 10 of the introducer 6.

As is explained in more detail below, during advancement of the protective sleeve 12, the moveable inner sleeve portion 22 is moved distally with respect to the introducer 6. At the crown region 14, this causes the moveable inner sleeve portion 22 to turn back on itself (i.e., a movement similar to a U-turn), in which the moveable inner sleeve portion 22 now becomes the stationary outer sleeve portion 16. During this advancement process, the crown region 14 as well as the protective sleeve 12 extend distally with respect to the introducer 6 so as to enable safe deployment of the catheter 20.

During retraction of the protective sleeve 12, the operation described above works in reverse. Namely, the moveable inner sleeve portion 22 is retracted in the proximal direction of the device 2 which causes the length of the protective sleeve 12 to shorten. In the retraction process, the outer sleeve portion 16 transitions to the inner sleeve portion 22 as the crown region 14 moves in the proximal direction.

Still referring to FIG. 1, an advancement/retraction mechanism 24 is disposed proximal to the introducer 6 and engages with the inner sleeve portion 22 of the protective sleeve 12. During advancement of the protective sleeve 12, the mechanism 24 acts as an advancement device for moving the inner sleeve portion 22 in the distal direction. This causes the protective sleeve 12 to be unfurled and deployed against the spinal cord 18. Similarly, during retraction, the mechanism 24 acts as a retraction device for moving the inner sleeve portion 22 in the proximal direction so as to retract the protective sleeve 12 into the device 2.

The advancement/retraction mechanism 24 preferably operates by frictionally engaging with the inner sleeve portion 22 of the protective sleeve 12. FIG. 1 shows cylindrically shaped rollers 26 that frictional engage with the inner sleeve portion 22 for advancing and retracting the protective sleeve 12. An excess amount 28 of protective sleeve 12 is shown in FIG. 1 proximal to the advancement/retraction mechanism 24 and is used when the protective sleeve 12 is advanced.

FIG. 1 also shows cylindrically shaped rollers 30 that frictionally engage with an outer surface of the catheter 20. The rollers 30 may be used to determine the rate at which the catheter 20 is advanced and retracted. It is also contemplated that the rollers 30 may also be used to advance and retract the catheter 20 through the protective sleeve 12. In this regard, the rollers 30 would be coupled to a suitable drive mechanism such as a motor or knob that could be manually turned to advance and retract the catheter. Alternatively, the rollers 30 may just be used to determine the rate of advancement or retraction between the catheter 20 and the protective sleeve 12. In this way, the catheter 20 can be advanced and retracted manually or a separate driving device might be employed.

Figure 2:
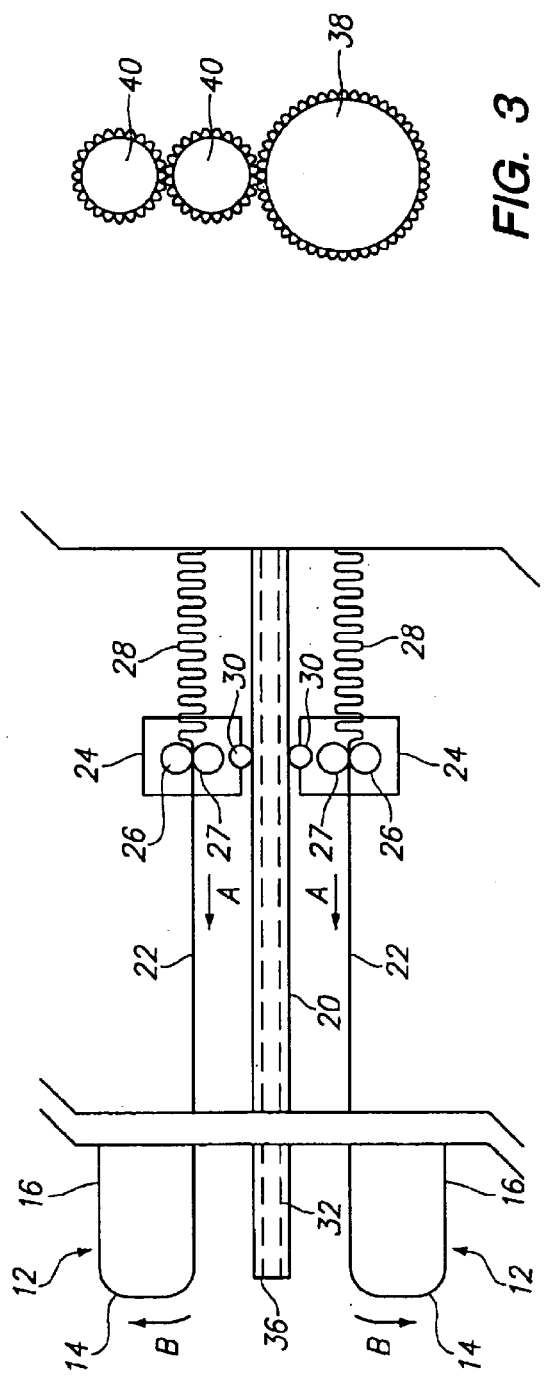
FIG. 2 is an enlarged side cross-sectional view of the device shown in FIG. 1.

FIG. 2 shows a close-up view of another example of an advancement/retraction mechanism 24 that may be used with the device 2. In this embodiment, a pair of rollers 26, 27 are used to impart motion to the inner sleeve portion 22. In FIG. 2, the protective sleeve 12 is shown advancing by arrows A. The transition of the inner sleeve portion 22 to the outer sleeve portion is seen by arrows B in the crown region 14.

Referring now to FIGS. 1 and 2, the device 2 also includes a catheter 20 contained inside the protective sleeve 12. The catheter 20 includes a lumen 32 (best shown in FIG. 2) through which a guidewire or other tubular members may pass. The catheter 20 is disposed adjacent to the inner sleeve portion 22 of the protective sleeve 12. The proximal end of the catheter 20 contains a hub 34. The catheter 20 is made of a flexible material that permits it to pass through the spinal canal 4. The catheter 20 includes a distally located tip 36 that is maneuvered through the spinal canal 4.

Figure 11:
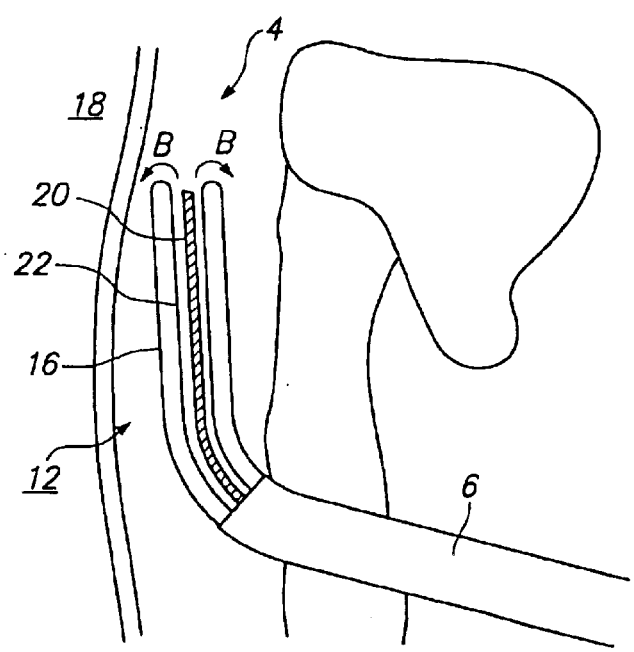
FIG. 11 is a magnified view of the distal end of the device shown in FIG. 10.

During advancement of the device 2, the distal tip 36 of the catheter 20 should never pass beyond (i.e. distal to) the crown region 14 of the protective sleeve 12. If the distal tip 36 of the catheter 20 were allowed to be exposed beyond the protective sleeve 12, the catheter 20 would contact and rub against the spinal cord 18, thereby increasing the risk of damage to the spinal cord 18. Consequently, the distal tip 36 of the catheter 20 should always be adjacent to (as shown in FIGS. 1, 2, and 11) or proximal to the crown region 14 of the protective sleeve 12.

Given this requirement, if both the catheter 20 and the protective sleeve 12 start at the same location and are each advanced in the distal direction, the inner sleeve portion 22 of the protective sleeve 12 needs to advance at rate that is at least twice the rate at which the catheter 20 is advanced. The at least 2× rate is required due to the folded structure of the protective sleeve 12. Essentially, twice the amount of distance needs to be covered by the inner sleeve portion 22 to keep up with the advancing catheter 20 of course, if the protective sleeve 12 is advanced first and then the catheter 20 is deployed, this rate requirement is not needed. The main requirement is that during advancement, the distal tip 36 of the catheter 20 should not be able to contact the spinal cord 18.

Figure 3:
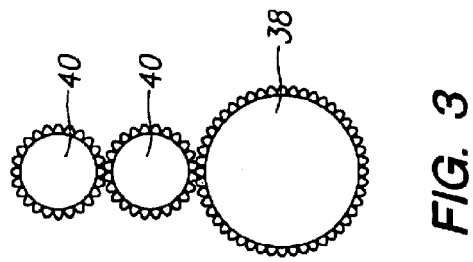
FIG. 3 shows a series of gears used to advance and retract the protective sleeve in one preferred embodiment of the invention.

FIG. 3 shows one embodiment used to create an advancement rate of the protective sleeve 12 that is at least twice the advancement rate of the catheter 20. In this embodiment, movement of the catheter 20 causes corresponding rotation of a catheter gear 38. The catheter gear 38 is meshed with a set of smaller protective sleeve gears 40 that, in turn, are mechanically connected to rollers 26, 27. The gearing is such that displacement of the catheter 20 causes a displacement of the protective sleeve 12 at a rate that is at least twice the rate of displacement of the catheter 20. Alternatively, there might only be a single gear for the protective sleeve 12 if only one roller 26 is used to feed the protective sleeve 12 (For example, as in shown in FIG. 1).

Figure 4A:
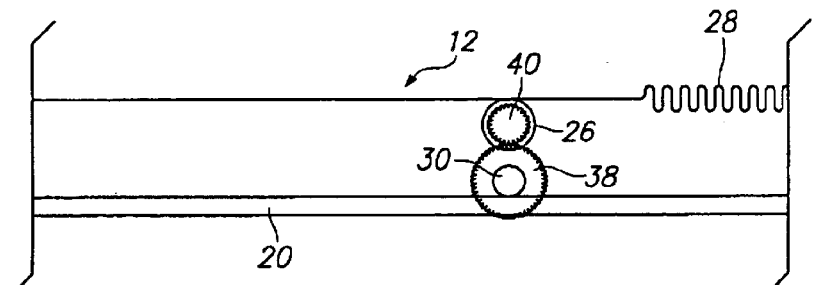
FIG. 4(a) illustrates a partial side view of an advancement mechanism used to advance the protective sleeve and catheter at a particular rate with respect to one another.
Figure 4B:
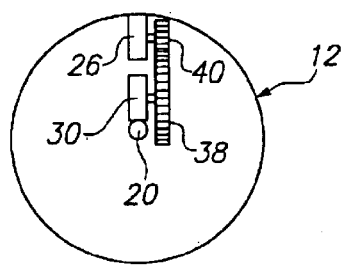
FIG. 4(b) illustrates an end view of the advancement mechanism shown in FIG. 4(a).

FIGS. 4(a) and 4(b) illustrate yet another preferred embodiment that is used to create an advancement rate of the protective sleeve 12 that is at least twice the advancement rate of the catheter 20. In this embodiment, movement of the catheter 20 causes corresponding rotation of a catheter gear 38 (alternatively, the catheter gear 38 can be driven by a motor (not shown)). The catheter gear 38 is mechanically connected to a roller 30 that frictionally engages with the catheter 20 body. The catheter gear 38 is meshed with a smaller protective sleeve gear 40, that, in turn, is mechanically connected to a roller 26 that frictionally engages with the protective sleeve 12. Preferably, the circumference of the catheter gear 38 is at least twice the circumference of the protective sleeve gear 40.

Figure 5:
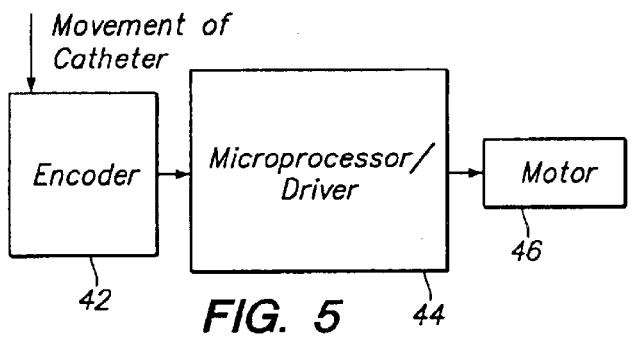
FIG. 5 shows a schematic representation of a microprocessor/drive circuit-based process that is used to advance and retract the protective sleeve in another preferred embodiment of the invention.

FIG. 5 illustrates another embodiment used to advance the protective sleeve 12 at a rate that is at least twice the rate of advancement of the catheter 20. An encoder 42 is used to measure the linear movement of the catheter 20. The encoder 42 may be coupled to a roller 30 or the like to determine the location and/or rate of advancement of the catheter 20. This information is then sent to a microprocessor/driver circuit 44 that controls the speed of a motor 46 that is coupled to the advancement/retraction mechanism 24. The microprocessor/driver circuit drives the motor 46 at a speed that creates an advancement rate in the protective sleeve 12 that is at least twice the advancement rate of the catheter 20. Preferably, this control system can be implemented on a real-time basis.

Figure 6:
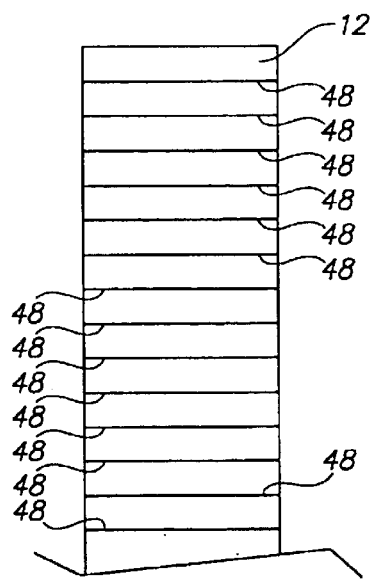
FIG. 6 shows a protective sleeve that has been cut axially along its length in its unfolded state so as to show pleats present in the protective sleeve.

FIG. 6 shows a preferred protective sleeve 12 that is used in the device 2. The protective sleeve 12 contains a plurality of pleats 48. The pleats 48 are longitudinally oriented along the length of the protective sleeve 12 and aid in the unfurling of the protective sleeve 12. Specifically, the pleats 48 help the inner sleeve portion 22 transition to the outer sleeve portion 16 during advancement. Similarly, the pleats 48 help the outer sleeve portion 16 transition to the inner sleeve portion 22 during retraction.

Figure 7:
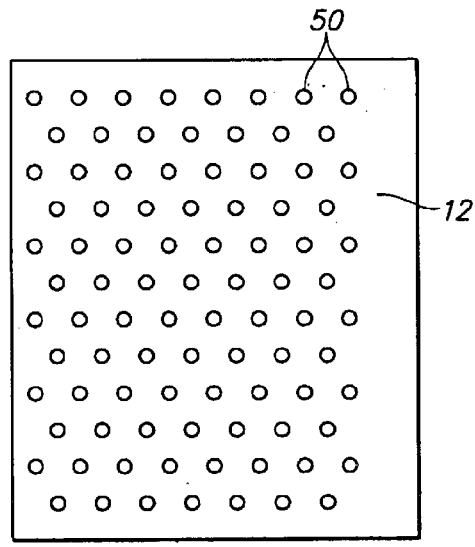
FIG. 7 shows a protective sleeve according to another preferred embodiment that has been cut axially along its length in its unfolded state. The protective sleeve contains a plurality of ports.

FIG. 7 shows an alternative embodiment of the protective sleeve 12. In this embodiment, a plurality of ports or holes 50 are present in the protective sleeve 12. The ports 50 allow fluid such as cerebrospinal fluid (CSF) to pass from one side of the protective sleeve 12 to the other. The ports 50 are preferably located along substantially if not the entire length of the protective sleeve 12. The ports 50 are small enough to prevent them from getting caught on material in the spinal canal 4. The ports 50, however, need to be large enough and evenly distributed so as to allow CSF to freely move between the catheter 20 and the protective sleeve 12. By allowing CSF fluid to cross the protective sleeve 12, friction is reduced between the inner and outer portions 22, 16 of the protective sleeve 12. Moreover, friction is reduced between the catheter 20 and the inner sleeve portion 22 of the protective sleeve 12. The ports 50 are particularly helpful when CSF fluid or other fluids are needed to active the hydrophilic coating that is present on the exterior of some catheters 20.

Figure 8:
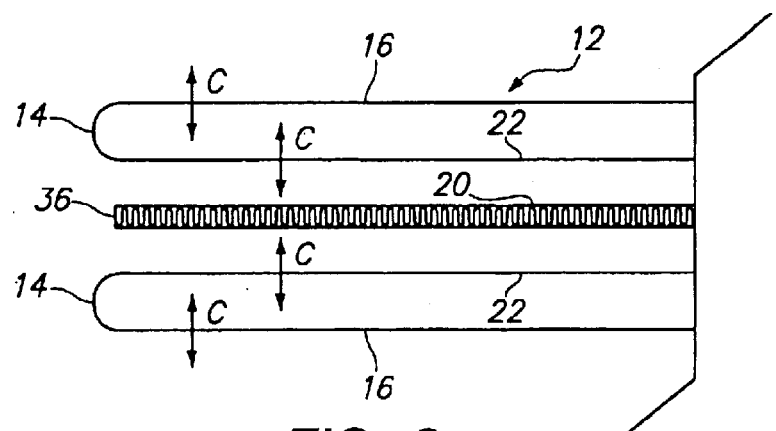
FIG. 8 shows a side cross-sectional view of the distal end the device using the protective sleeve shown in FIG. 7.

FIG. 8 shows a magnified view of the distal end of the device 2 using a protective sleeve 12 with ports 50. The arrows C represent the migration of CSF fluid across the protective sleeve 12. CSF fluid is thus present between the inner and outer portions 22, 16 of the protective sleeve 12 as well as between the catheter 20 and the inner sleeve portion 22 of the protective sleeve 12.

Figure 9:
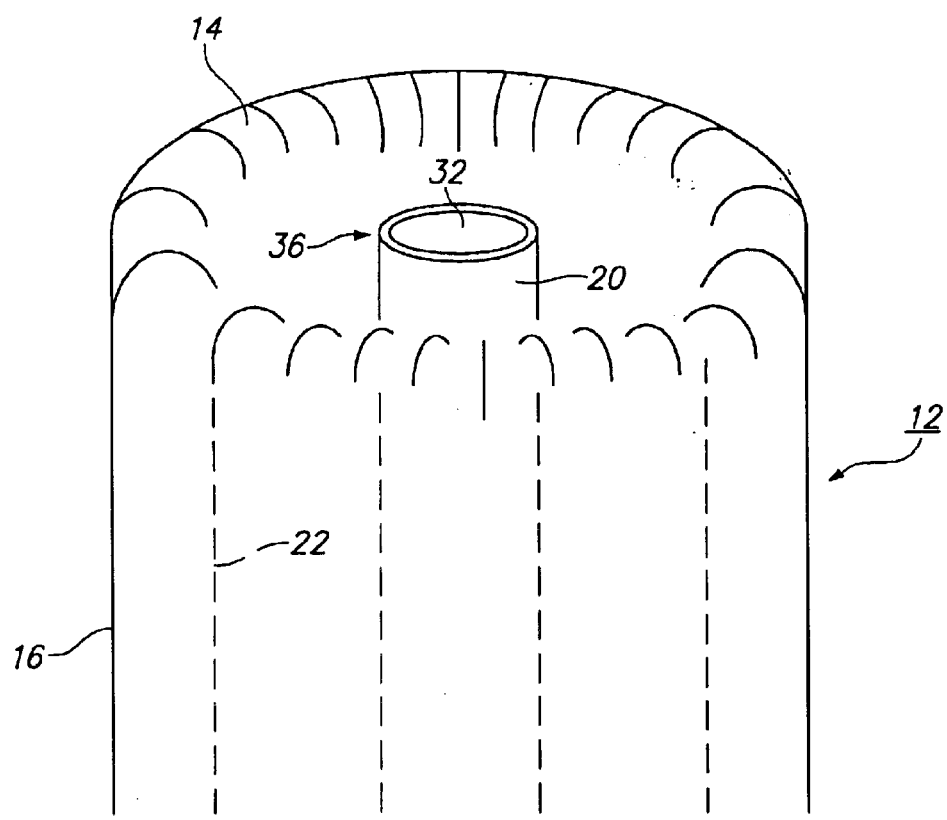
FIG. 9 shows a perspective view of the distal end of the device, including the protective sleeve and the catheter disposed inside thereof.

FIG. 9 shows a perspective view of the distal end of the device 2, including the distal tip 36 of the catheter 20 and the crown region 14. The distal tip 36 of the catheter 20 is shown adjacent to the crown region 14.

Figure 10:
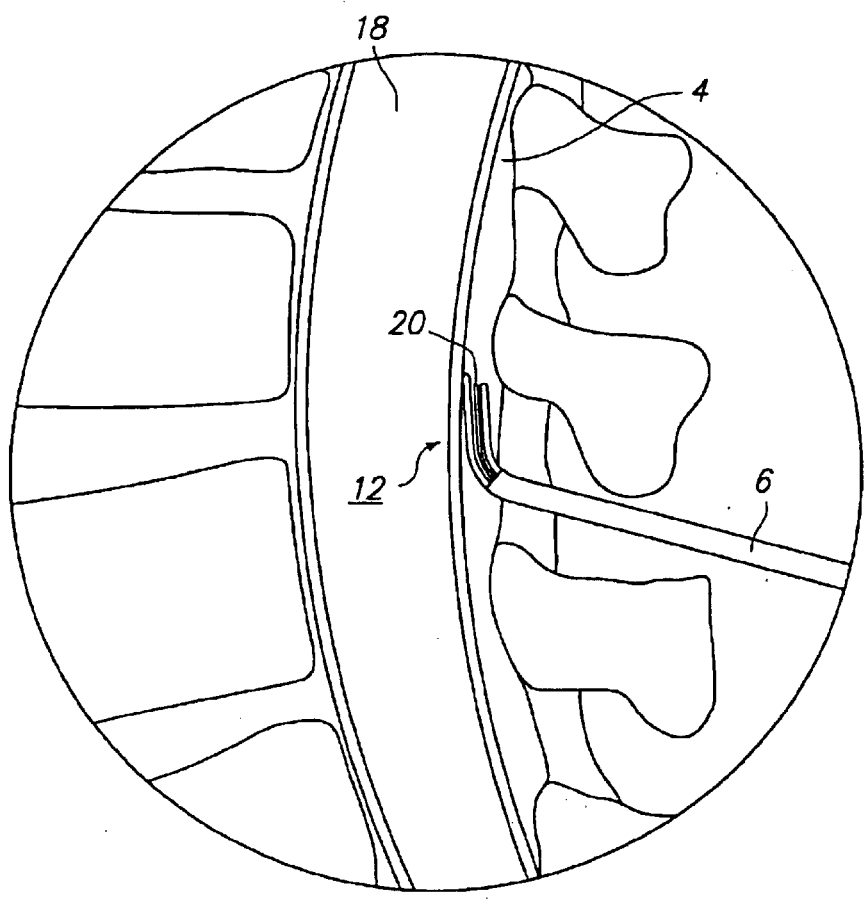
FIG. 10 illustrates the spinal canal access device entering the epidural space of a patient.

FIGS. 10 and 11 show actual implementation of the device 2 within a patient's spinal canal 4. First, a needle (not shown) is inserted into the patient's back into the epidural space between two adjacent vertebra. Next, the introducer 6 is introduced over the needle into its final position and the needle is removed. The device 2 is ready now for the deployment of the protective sleeve 12 and the catheter 20. FIGS. 10 and 11 show the protective sleeve 12 and the catheter 20 being advanced upwards within the spinal canal 4. The protective sleeve 12 is advanced at a rate so as to keep the distal tip 36 of the catheter 20 within the inner sleeve portion 22 of the protective sleeve 12. As seen in FIGS. 10 and 11, the protective sleeve 12 forms a stationary physical barrier between the spinal cord 18 and the catheter 20. The protective sleeve 12 thus protects the spinal cord 18 from being nicked or rubbed by the moving catheter 20.

The protective sleeve 12 and catheter 20 are moved up the spinal canal 4 until the desired location is reached. For example, for access to the vasculature of the brain, the protective sleeve 12 and catheter 20 may stop just below the brain. At this point a guidewire, microcatheter, or the like can be introduced into the lumen 32 of the catheter 20 and advanced to the area of interest.

The device 2 can be used in any number of ways. First, the device 2 can be used for the delivery of an imaging device (ultrasound-based, optical coherence tomography-based) to a region of the spinal canal 4 or brain. The device 2 might also be used to manage fluids in the region surrounding the brain. For example, the device 2 can be used to control the temperature of certain regions of the brain. The device 2 might also be used in vascular surgery within the brain. In yet another use, the device 2 could be employed to delivery drugs to specific locations within the spinal canal 4 or brain. Essentially, the device 2 can be used in any procedure that uses the spinal canal 4 as a passageway for a catheter 20.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the spirit and scope of the appended claims.

What is claimed is:

1. A device comprising:
    an introducer having proximal and distal ends;
    a protective sleeve having one end attached to the distal end of the introducer, the sleeve having an outer stationary portion and an inner moveable portion; and
    a catheter disposed within the protective sleeve adjacent to the moveable portion, the catheter having a distal end that is movable relative to a proximal end of the movable portion.

2. The device according to claim 1, further comprising a crown region located between the outer stationary portion of the protective sleeve and the moveable inner portion of the protective sleeve.

3. The device according to claim 1, further comprising an advancement mechanism for advancing the protective sleeve within the spinal canal.

4. The device according to claim 1, further comprising a retraction mechanism for retracting the protective sleeve within the spinal canal.

5. The device according to claim 3, wherein the advancement mechanism advances the protective sleeve at a rate that is at least twice the advancement rate of the catheter.

6. The device according to claim 4, wherein the retraction mechanism retracts the protective sleeve at a rate that is at least twice the retraction rate of the catheter.

7. The device according to claim 2, wherein the distal tip of the catheter is disposed adjacent to the crown region during advancement.

8. The device according to claim 2, wherein the distal tip of the catheter is disposed proximal to the crown region during advancement.

9. The device according to claim 1, wherein the protective sleeve includes a plurality of ports in the outer stationary portion and the inner moveable portion.

10. The device according to claim 1, wherein the catheter includes a lumen therethrough.

11. The device according to claim 3, wherein the advancement mechanism comprises a motor.

12. The device according to claim 4, wherein the retraction mechanism comprises a motor.

13. The device according to claim 3, wherein the advancement mechanism also advances the catheter.

14. The device according to claim 4, wherein the retraction mechanism also retracts the catheter.

15. The device according to claim 1, the protective sleeve including a series of longitudinal pleats.

16. A device comprising:

an introducer having proximal and distal ends;

a protective sleeve having a first end and a second end, the first end attached to the distal end of the introducer, the protective sleeve projecting distally so as to form a moveable crown region at the distal end; and a catheter disposed within the protective sleeve, the catheter having a distal end that is movable relative to the second end of the protective sleeve.

17. The device according to claim 16, wherein the distal tip of the catheter is disposed adjacent to the moveable crown region.

18. The device according to claim 16, wherein the distal tip of the catheter is disposed proximal to the moveable crown region.

* * * * *